United States Patent
Tasca

(10) Patent No.: US 6,534,976 B2
(45) Date of Patent: Mar. 18, 2003

(54) DEVICE HAVING ACTIVE AND REFERENCE COILS FOR PERFORMING NON-DESTRUCTIVE INSPECTION BY EDDY CURRENT

(75) Inventor: Jean-Pierre Tasca, Sainte Genevieve des Bois (FR)

(73) Assignee: Cegelec, Rueil-Malmaison (FR)

( * ) Notice: Subject to any disclaimer, the term of this patent is extended or adjusted under 35 U.S.C. 154(b) by 41 days.

(21) Appl. No.: 09/809,264

(22) Filed: Mar. 16, 2001

(65) Prior Publication Data

US 2002/0027437 A1 Mar. 7, 2002

(30) Foreign Application Priority Data

Mar. 23, 2000 (FR) .............................. 00 03731

(51) Int. Cl.[7] .......................... G01N 27/82; G01N 27/90
(52) U.S. Cl. ...................................... 324/238; 324/220
(58) Field of Search ................................ 324/220, 221, 324/228, 236–243

(56) References Cited

U.S. PATENT DOCUMENTS

| | | | |
|---|---|---|---|
| 4,635,832 A | 1/1987 | Angerer et al. | |
| 4,893,079 A | * 1/1990 | Kustra et al. | 324/225 |
| 4,906,927 A | * 3/1990 | Urata et al. | 324/233 |
| 5,083,468 A | 1/1992 | Dobler et al. | |
| 5,172,058 A | 12/1992 | Tasca | |
| 6,051,972 A | * 4/2000 | Bour et al. | 324/230 |

* cited by examiner

Primary Examiner—Jay Patidar
(74) Attorney, Agent, or Firm—Sughrue Mion, PLLC

(57) ABSTRACT

A device for inspecting a part by eddy currents, the device comprising at least one measurement bridge having an active coil which is connected between a first terminal and a second terminal, and a reference circuit which is connected between said second terminal and a third terminal, said first and third terminals being for connection to an AC voltage generator so that an alternating magnetic field is generated by the active coil in the part to be inspected in order to enable any variation in the impedance of the active coil on passing over a defect in a part under inspection to be detected by analyzing an output voltage of the device, wherein the reference circuit is a reference coil identical to the active coil, wherein the first terminal and the third terminal are for receiving voltages applied by the AC voltage generator which are equal in value and of opposite signs relative to a neutral phase of said generator, the output voltage being the voltage read between said second terminal and said neutral phase, and wherein the reference coil is electromagnetically isolated from the part to be inspected.

6 Claims, 4 Drawing Sheets

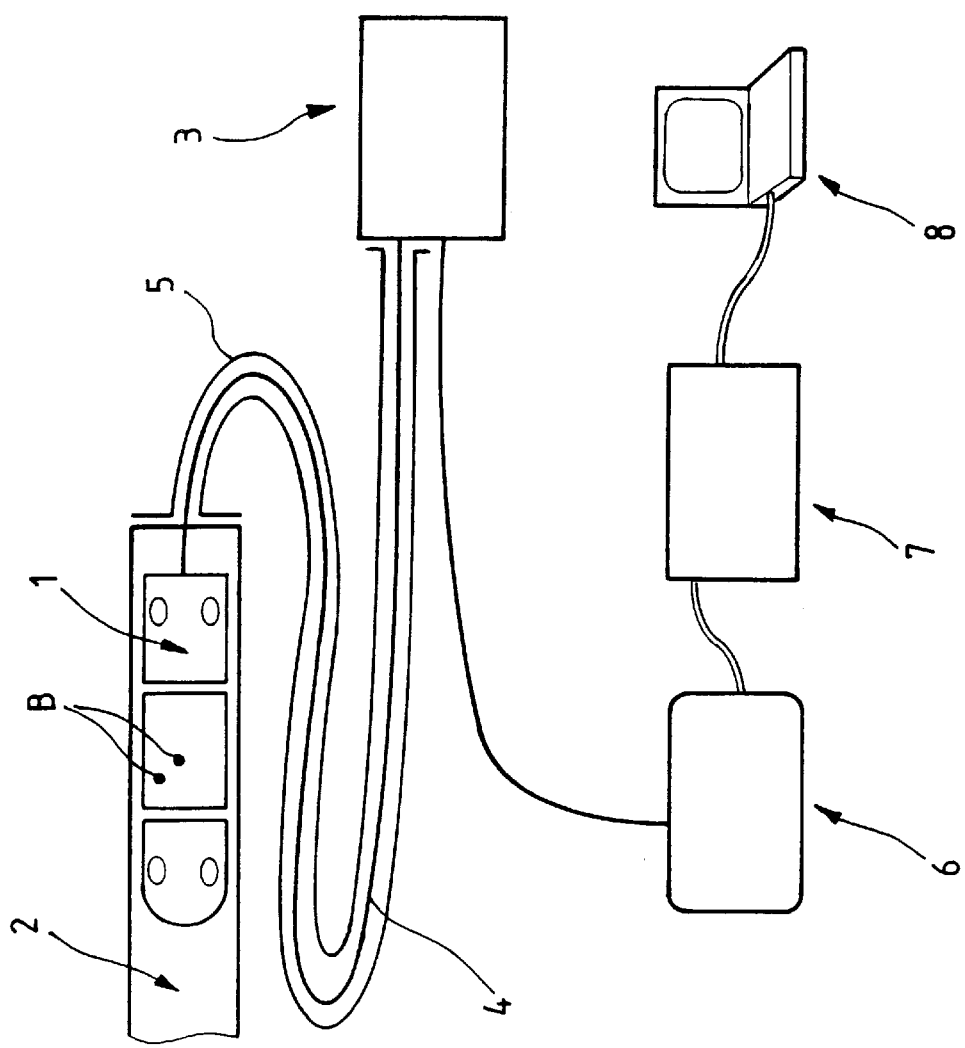
FIG_1

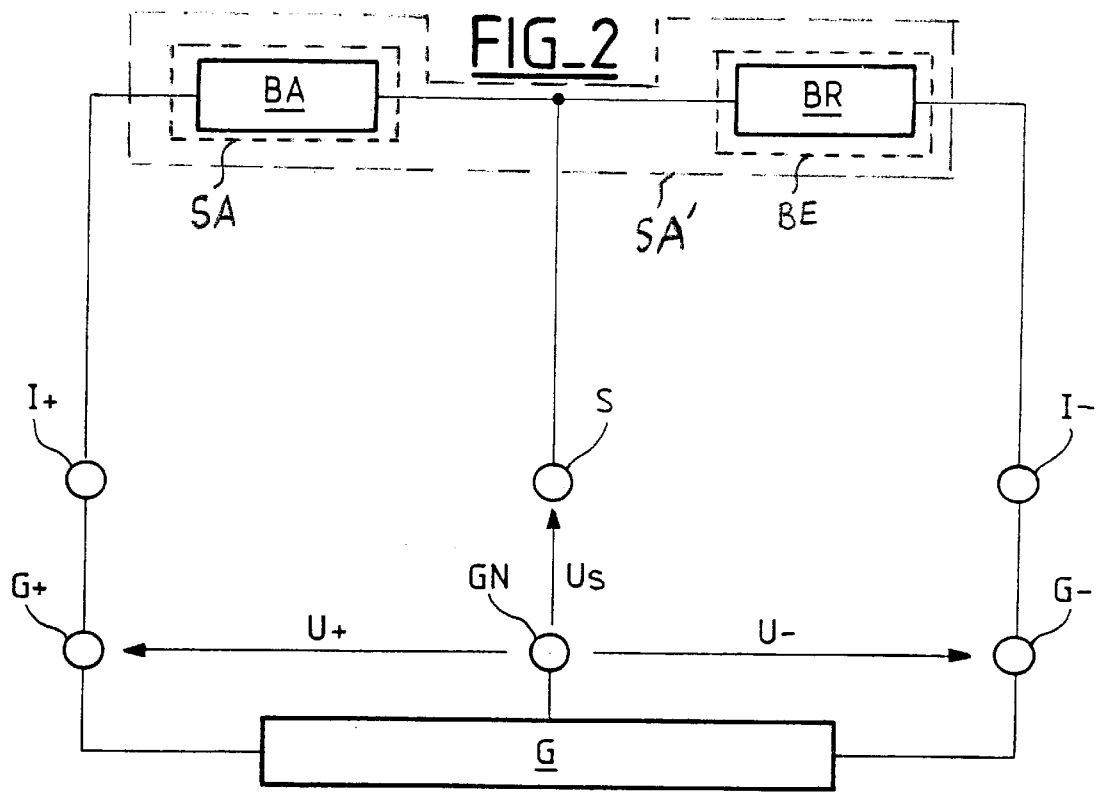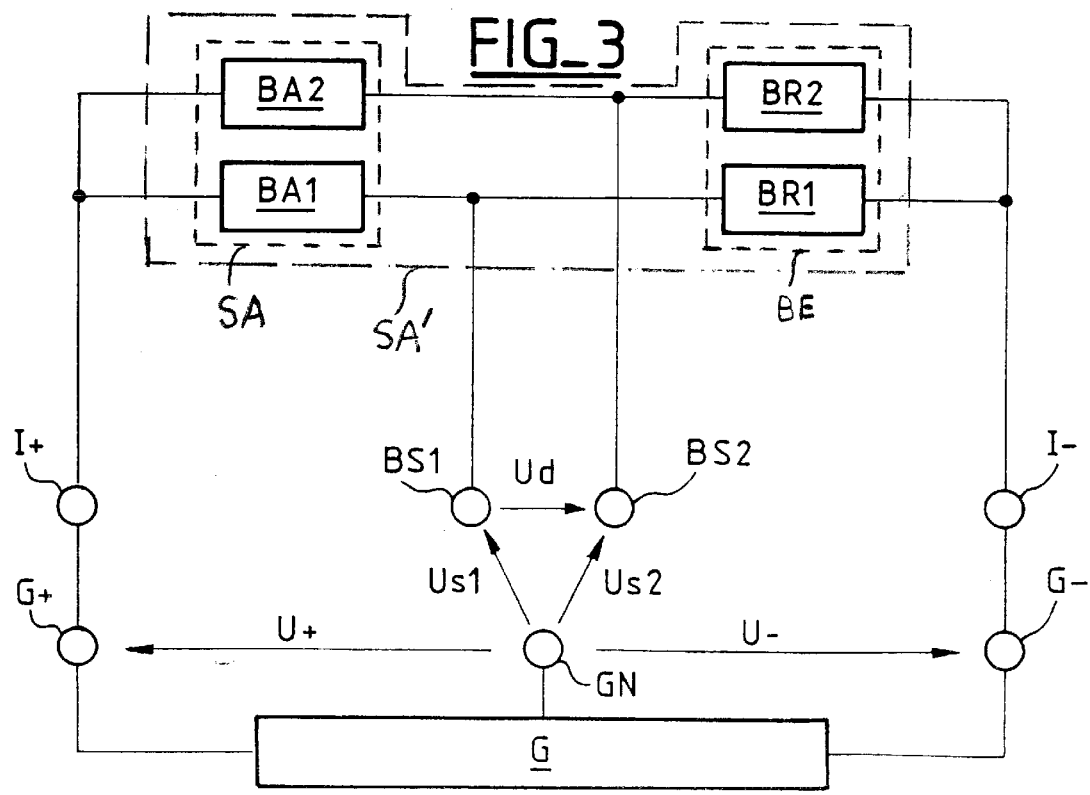

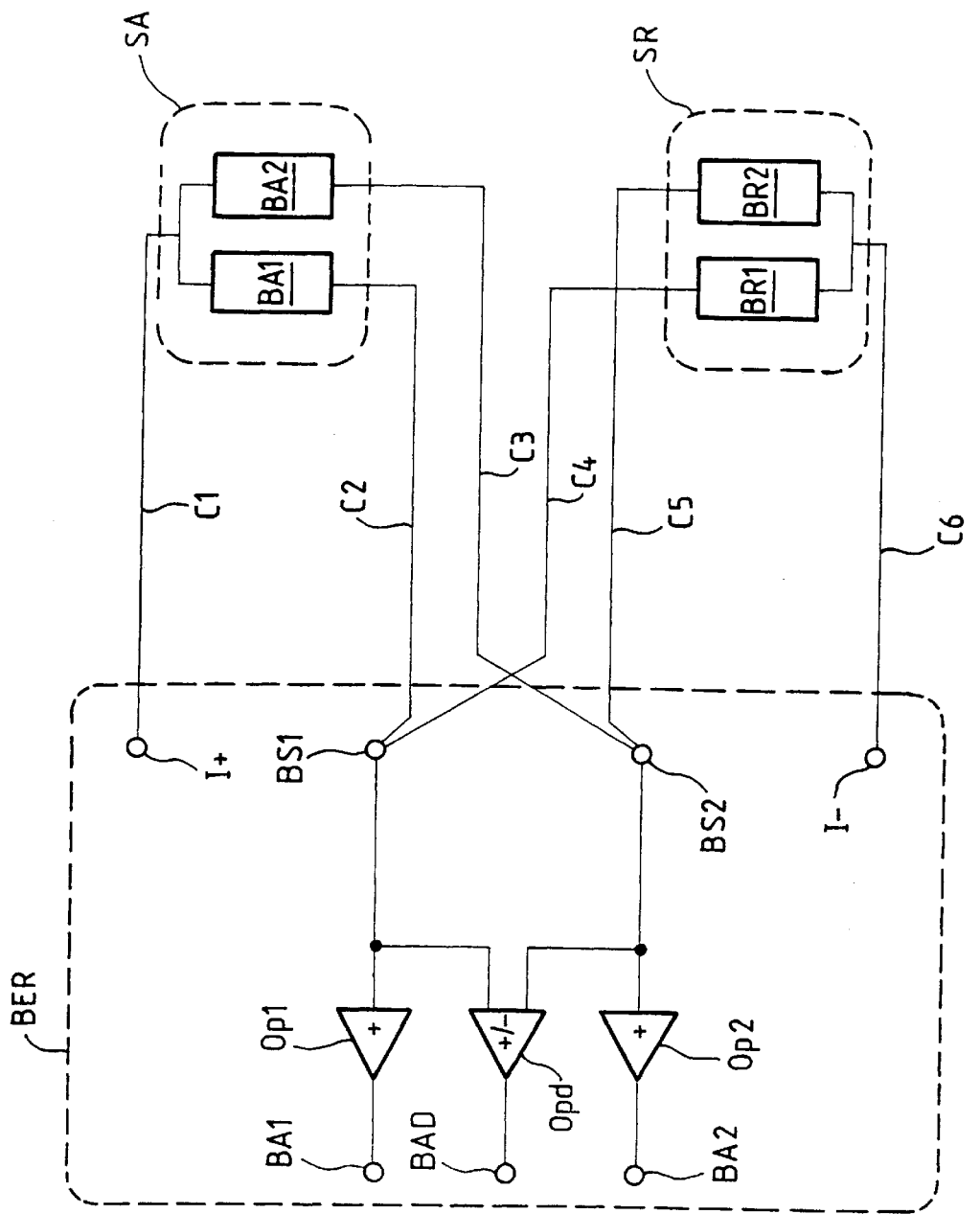
FIG_4

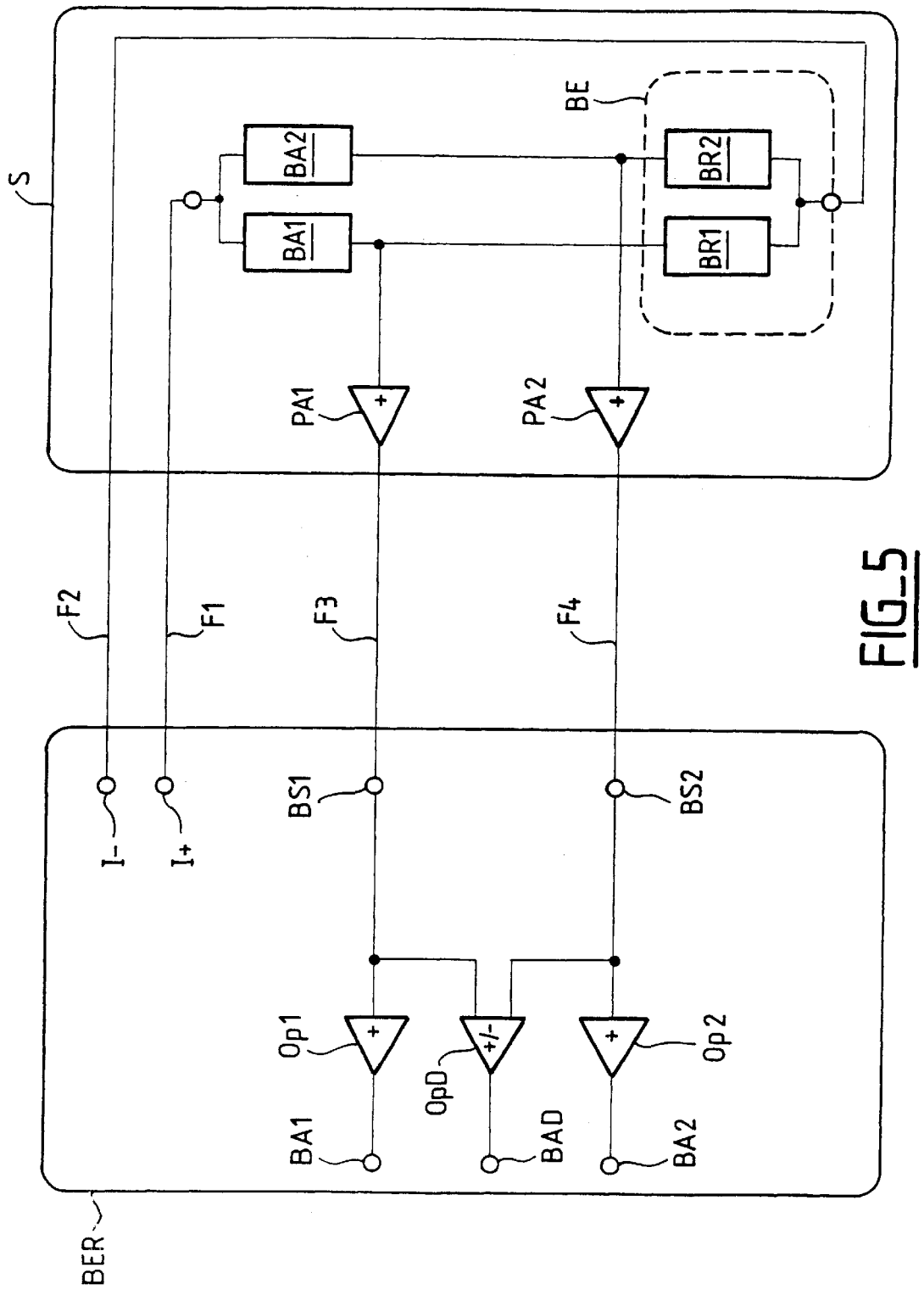
FIG_5

DEVICE HAVING ACTIVE AND REFERENCE COILS FOR PERFORMING NON-DESTRUCTIVE INSPECTION BY EDDY CURRENT

The invention relates to a device for inspecting parts by eddy currents, the device comprising at least one measurement bridge having an active coil which is connected between a first terminal and a second terminal, and a reference circuit which is connected between said second terminal and a third terminal, said first and third terminals being for connection to an AC voltage generator so that an alternating magnetic field is generated by the active coil in a part to be inspected in order to enable any variation in the impedance of the active coil on passing over a defect in a part under inspection to be detected by analyzing an output voltage of the device.

BACKGROUND OF THE INVENTION

Non-destructive inspection by means of eddy currents is in widespread use in industry for verifying the mechanical state of metal parts, since such testing enables irregularities such as break starters and surface state defects in such parts to be detected. By using an active coil to give rise to an alternating magnetic field in a metal part, currents are caused to flow in said part which modify the magnetic field induced by the coil, and this modification to the magnetic field is reflected by a modification in the impedance of the active coil.

By way of example, in the steam generators of nuclear power stations, the pipework which operates under severe conditions of temperature and pressure needs to be inspected regularly. Such generators typically comprise a support plate having a multitude of U-shaped tubes inserted therein, with heat exchange taking place via the tubes. Such tubes are suitable for being inspected by eddy currents. Their accessibility means that it is possible to insert a probe containing an active coil, and to move the coil while it is generating an alternating magnetic field. Simultaneously, by analyzing an output voltage, it is possible to detect any variation in the impedance of the active coil as it passes over a defect in the part. In such inspection, it is particularly advantageous to perform measurements of a given portion of tube at a plurality of frequencies in order to evaluate a magnitude concerning the size of the defect whose shape is to be discovered. This type of measurement is particularly useful for inspecting tube portions that are inserted in a support plate since they enable the influence of the plate to be distinguished from the influence of the tube itself.

Depending on circumstances, conventional inspection devices comprise either a single bridge for performing measurements in a so-called "absolute" mode, or a plurality of bridges for performing measurements both in differential mode and in absolute mode. In general, a measurement bridge comprises a first terminal connected to the active coil, referred to as the positive injection terminal; a second terminal connected to the active coil and to the reference circuit, referred to as the output terminal; and a third terminal connected to the reference circuit and referred to as the negative injection terminal.

For an inspection device comprising a single bridge, and thus supplying a single output voltage, the active coil placed in a probe body is connected in series with a reference circuit so as to constituted a measurement bridge. The bridge constituted in this way is powered between its positive and negative injection terminals by an AC voltage generator, and the output voltage from the device is the voltage read between the output terminal and the negative injection terminal, which is usually connected to ground. In such a device, the reference circuit conventionally used is a resistor whose impedance at the working frequency is close to that of the active coil. Thus, the form of the output voltage is close to half the power supply voltage when the bridge is in balance, and it departs significantly therefrom when the bridge is out of balance. To perform inspection in absolute mode, the probe is moved inside the tube to be inspected, and the output voltage which has a certain form (amplitude and phase shift) for a good portion of tube departs from said form when the active coil passes over a defect.

In terms of orders of magnitude, it should be observed that the output voltage obtained has a mean value which is of the order of a few volts, whereas the variations which appear are of the order of a few millivolts. It is therefore essential to have signal processing means to filter the output voltage and to amplify those components therein that are meaningful so as to show up any variation in the impedance of the coil. To do this, use is made of a synchronous demodulation that is capable of operating in real time and of supplying data which a computer records, likewise in real time.

U.S. Pat. No. 4,635,832 describes a method and apparatus for casting molten metal covered in a layer of slag from a ladle into a tundish. The bottom of the ladle is connected to the tundish via a tube through which the molten metal flows. That document describes a measuring circuit for detecting the passage of slag along the tube connecting the ladle to the tundish: the tube is surrounded by two coils that are connected in series and that extend one after the other along the tube. The coils are fed from the secondary of a transformer that itself comprises two coils in series, forming a Wheastone bridge.

The measurement diagonal is taken between the point interconnecting the two coils surrounding the tube and the point interconnecting the two coils of the secondary of the transformer. If any slag passes along the tube connecting the ladle to the tundish, then the output signal is observed to vary due to the coil which is affected by said passage having its impedance modified. Nevertheless, by mutual inductance between the two coils, the other coil is also affected and therefore cannot constitute a reference coil.

OBJECTS AND SUMMARY OF THE INVENTION

The present invention proposes a device in which, in the absence of any fault, the output signal is close to zero and in which the reference coil is protected from the influences of the part under inspection.

The invention thus provides a device for inspecting a part by eddy currents, the device comprising at least one measurement bridge having an active coil which is connected between a first terminal and a second terminal, and a reference circuit which is connected between said second terminal and a third terminal, said first and third terminals being for connection to an AC voltage generator so that an alternating magnetic field is generated by the active coil in the part to be inspected in order to enable any variation in the impedance of the active coil on passing over a defect in a part under inspection to be detected by analyzing an output voltage of the device, wherein the reference circuit is a reference coil identical to the active coil, wherein the first terminal and the third terminal are for receiving voltages applied by the AC voltage generator which are equal in value and of opposite signs relative to a neutral phase of said generator, the output voltage being the voltage read between said second terminal and said neutral phase, and wherein the reference coil is electromagnetically isolated from the part to be inspected.

According to another characteristic, the device comprises a plurality of measurement bridges having common respective first terminals, common respective third terminals, and different second terminals, thereby obtaining an output voltage for each measurement bridge which is read between the second terminal of the corresponding bridge and the neutral phase of the AC voltage generator.

In a first embodiment, the active coil(s) is/are situated in a probe body, the reference coil(s) being situated outside the probe body and being remote from the part under inspection.

In a second embodiment, the active coil(s) and the reference coil(s) are situated in a single probe body, the reference coils being isolated by electromagnetic shielding.

According to another characteristic, the second terminal of each measurement bridge is connected to at least one operational amplifier.

With this arrangement, the output voltage is very close to zero if the bridge is in balance since it is close to the sum of the injection voltages which are opposite at a given instant. Thus, the output voltage that is obtained does not need any special filtering so it can be amplified directly prior to demodulation. With such a device, it is possible to obtain a raw signal-to-noise ratio of about 40 dB, which represents a significant improvement over the 25 dB provided by a conventional device.

Another advantage of the device of the invention is that it is capable of operating at a plurality of frequencies without any need to change the reference circuit. This characteristic is particularly advantageous since units are available on the market comprising a voltage generator and a synchronous demodulator that are capable of operating in real time at a plurality of frequencies: with such a unit, it is possible to inject an AC voltage into the device that is made up of a plurality of voltages at different frequencies, and to demodulate each output voltage as a plurality of voltages each corresponding to one of the injected frequencies. As can be seen, associating such a unit with the device of the invention makes it possible to perform measurements at a plurality of different frequencies on a single passage of the probe in the part.

BRIEF DESCRIPTION OF THE DRAWINGS

Embodiments of the device of the invention are described below and shown in the accompanying figures.

FIG. 1 is an overall view of apparatus in which the device of the invention is mounted.

FIG. 2 is a block diagram of a first embodiment of the device of the invention.

FIG. 3 is a block diagram of a second embodiment of the device of the invention.

FIG. 4 is a block diagram of a third embodiment of the device of the invention.

FIG. 5 is a block diagram of a fourth embodiment of the device of the invention.

MORE DETAILED DESCRIPTION

In FIG. 1, the device for inspecting parts by means of eddy currents comprises a probe 1 in which at least one coil is placed, and in the present case in which two coils are placed. The probe 1 is moved in translation and in rotation in a tube 2 to be inspected by means of a unit 3 acting via a first sheath 4 containing electric cables and rigidly connected both to the probe body 1 and to a moving portion of the unit 3. This first sheath 4 slides inside a sheath 5 which is rigidly connected firstly to the tube under inspection and secondly to the structure of the unit 3. In this arrangement, the unit 3 drives its moving portion in translation and in rotation, with this movement being transmitted to the probe 1 by means of the sheath 4, such that the path followed by an active coil of the probe is a helix which travels along the entire surface of the portion of tube to be inspected. The unit 3 is connected to a unit 6 which contains operational amplifiers and which transmits the excitation voltage to the probe via the unit 3, and which receives therefrom each of the output voltages which it amplifies. The unit 6 optionally contains each reference coil and is in turn connected to a unit 7 which has an AC voltage generator and a synchronous demodulator. With this arrangement, the unit 6 receives the injection voltage of the device from the unit 7 and supplies it with each amplified output voltage for demodulation. Finally, a computer 8 is connected to the unit 7 so as to control inspection and record the data provided by the synchronous demodulator contained in the unit 7.

FIG. 2 shows the elements of the device in a particular embodiment of the invention: a voltage generator G applies an AC voltage U+ between its positive terminal G+ and its neutral terminal GN, and another AC voltage U− between its negative terminal G− and its neutral terminal GN. The AC voltages U+ and U− are equal and in phase opposition. A measurement bridge mainly comprises terminals I+, I−, and S, the terminals I+ and I− being connected respectively to the terminals G+ and G− of the generator, with the measurement bridge further comprising an active coil BA connected to the terminal I+ and to the terminal S, and a reference coil BR connected to the terminal S and to the terminal I−. As can be seen in the figure, the output voltage Us is read between the terminal S of the bridge and the neutral terminal GN of the voltage generator.

When the probe body SA which contains the coil BA is moved in the tube to be inspected, the bridge has a certain small unbalance voltage which remains constant (in phase shift and in amplitude) so long as the probe lies in a good zone of the part, and which changes when the probe is close to a defect in the part.

The reference coil BR is situated outside the probe body SA and is remote from the part under inspection so as to isolate the part under inspection electromagnetically.

It is also possible to place the reference coil BR in the probe body SA' and to isolate it electromagnetically by means of electromagnetic shielding BE.

FIG. 3 shows the wiring of a device of the invention for performing measurements simultaneously in differential mode and in absolute mode. This device mainly comprises two measurement bridges which are connected in parallel to a common AC voltage generator. More particularly, the generator G has its positive output terminal G+ connected to the common positive injection terminal I+ and its negative output terminal G− connected to the common negative injection terminal I−. The first bridge is constituted by an active coil BA1 connected firstly to the common positive injection terminal I+ and secondly to an output terminal BS1, and a reference coil BR1 connected firstly to the output terminal BS1 and secondly to the negative injection terminal I−. In a similar configuration, a second bridge is made up of coils BA2 and BR2 connected to the injection terminals I+, I− and to BS2 which is the output terminal of the second bridge. These two bridges which are connected to the output terminals BS1 and BS2 make it possible together with the neutral GN of the generator to provide three output voltages: Us1 and Us2 which are the absolute output voltages from each of the bridges, and Ud which is the differential voltage between the two bridges. Us1 is thus the voltage read between BS1 and GN, Us2 is the voltage read between BS2 and GN, and Ud is the voltage read between BS1 and BS2.

As mentioned above, in such a device, the two active coils BA1 and BA2 are placed side by side in a probe body SA: if each of them lies over a good zone of the part being inspected, then the differential voltage Ud is very close to zero; if one of them is over a good zone and the other over a zone that includes a defect, then the bridge is out of balance and the voltage Ud becomes non-zero. In this case also, the reference coils BR2 and BR1 lie outside the probe body SA and are remote from the part to be inspected, or else they are situated in the probe body SA' and are isolated by electromagnetic screening BE.

FIG. 4 is a diagram showing an embodiment of a device of the invention that comprises two measurement bridges connected in parallel, for the case where the reference coils are not situated in the probe body containing the active coils: the lengths of the cables are selected in such a manner as to further reduce the effect of electromagnetic disturbances on the device; and the output voltages are amplified. In this device, the two active coils BA1 and BA2 are placed in a first probe body SA and the two reference coils BR1 and BR2 are placed in a second probe body SR, the set of output and injection terminals and the amplification portion being placed in a transceiver unit BER, which unit corresponds to the unit 6 in FIG. 1. In this arrangement, the probe body SA is connected to the unit BER by a first sheath containing cables C1, C2, and C3, and in similar manner the probe body SR is connected to the unit BER by a second sheath containing the cables C4, C5, and C6.

More particularly, the cable C1 is connected between the positive injection terminal I+ of the device situated in the unit BER and the active coils BA1 and BA2 situated in the probe body SA. The cable C2 is connected between the active coil BA1 and the output terminal BS1 situated in the unit BER. The cable C3 is connected between the active coil BA2 and the output terminal BS2 which is situated in the unit BER. In similar manner, the cables C4 and C5 connect the reference coils BR1 and BR2 respectively to their output terminals BS1 and BS2. Finally, the cable C6 is connected between the reference coils BR1 and BR2 situated in the probe body SR, an the negative injection terminal I– situated in the unit BER. In this arrangement, a device is thus obtained which has two measurement bridges connected in parallel between the injection terminals of the device, and for which the lengths of cable used for connecting the probe body having the active coils are identical to the lengths used for connecting the probe body containing the reference coils since all of the cables C1, C2, C3, C4, C5, and C6 are of the same length.

The advantage of such a configuration is that for practical reasons, during an inspection, the probe body containing the active coils is situated at about 10 meters from the devices for controlling and analyzing the signal which are connected to the unit BER, and it is then advantageous to place the probe body containing the reference coils at the same distance. By placing the probe body SR containing the reference coils at the same distance from the transceiver unit and using the same length of cabling as for the probe body containing the active coils, the effects of the electromagnetic disturbances to which the device is subjected are canceled at the amplified differential output terminal BAD of the device.

For amplification purposes, operational amplifiers Op1, Op2, and Opd are shown having their inputs connected respectively to the terminals BS1, BS2, and both BS1 and BS2, with their respective outputs being connected to terminals BA1, BA2, and BAD. In this way, the amplified output voltages can be used directly by the asynchronous demodulator from the terminals BA1, BA2, and BAD.

FIG. 5 is a diagram showing a device of the invention in which most of the components are integrated in the probe body, thus making it possible to reduce electromagnetic disturbances while conserving cabling which remains simple since it has only four long cables instead of the six cables included in the device shown in FIG. 4, said cables now additionally being all contained in the same sheath.

In this particular embodiment, a single probe body S contains: two active coils BA1 and BA2; two reference coils BR1 and BR2 which are isolated by electromagnetic shielding BE; and two operational amplifiers PA1 and PA2 for preamplifying the output voltages from the probe. This probe is connected to a transceiver unit by cables F1, F2, F3, and F4.

More particularly, the cable F1 is connected between the active coils BA1 and BA2, and a positive injection terminal I+ of the device situated in the unit BER. Similarly, the cable F2 is connected between the reference coils BR1 and BR2 and a negative injection terminal I– of the device situated in the unit BER. The operational amplifier PA1 is connected firstly to the coils BA1 and BR1, and secondly to the cable F3 which is connected to the output terminal BS1 situated in the unit BER. Similarly, the amplifier PA2 is connected firstly to the coils BA2 and BR2 and secondly to the cable F4 which is connected to the output terminal BS2 situated in the unit BER. In this arrangement, a device is thus obtained which has two measurement bridges connected in parallel between the injection terminals of the device.

Such an arrangement has multiple advantages: the lengths of cable used for connecting the active coils and the reference coils are identical, thereby reducing the effect of the electromagnetic disturbances to which the device is subjected, and in addition all of the cables are contained in the same sheath; integrating the reference coils in the probe body makes it possible to cancel the effects of temperature drift; finally, preamplification of the output voltages within the probe makes it possible to further increase the signal-to-noise ratio of the device.

To amplify the output voltages, there are three operational amplifiers Op1, Op2, and Opd as in the configuration of FIG. 4, these operational amplifiers being situated in the unit BER and having their inputs respectively connected to the terminals BS1, BS2, and both BS1 and BS2, and having their outputs connected respectively to the terminals BA1, BA2, and BAD. These amplifiers enable amplified output voltages to be obtained which can be used directly by the asynchronous demodulator, connected to the terminals BA1, BA2, and BAD.

The invention is not restricted solely to the embodiments described above, and can also be applied to using eddy currents to inspect any part having a surface of constant thickness or having appropriate geometrical qualities. Thus, for example, the invention is highly suitable for use in inspecting a metal plate of constant thickness.

What is claimed is:

1. A device for inspecting a part by eddy currents, the device comprising at least one measurement circuit including an active coil which is connected between a first terminal and a second terminal, and a reference circuit which is connected between said second terminal and a third terminal, said first and third terminals being for connection to an AC voltage generator so that an alternating magnetic field is generated by the active coil in the part to be inspected in order to enable any variation in the impedance of the active coil on passing over a defect in a part under inspection to be detected by analyzing an output voltage of the device, wherein the reference circuit is a reference coil identical to the active coil, wherein the first terminal and the third terminal receive voltages applied by the AC voltage generator which are equal in value and of opposite signs relative to a neutral phase of said generator, and the output voltage is the voltage read between said second terminal and said neutral phase, and wherein the reference coil is electromagnetically isolated from the part to be inspected.

2. A device according to claim 1, further comprising a plurality of measurement circuits having common respective first terminals, common respective third terminals, and different second terminals, thereby obtaining an output voltage for each measurement circuit which is read between the second terminal of the corresponding circuit and the neutral phase of the AC voltage generator.

3. A device according to claim 2, in which the second terminal of each measurement circuit is connected to at least one operational amplifier.

4. A device according to claim 3, in which each active coil, each reference coil, and operational amplifiers are integrated in a common probe body.

5. A device according to claim 1, wherein the active coil is situated in a probe body, and the reference coil is situated outside the probe body and remote from the part under inspection.

6. A device according to claim 1, wherein the active coil and the reference coil are situated in a single probe body, and the reference coil is isolated by electromagnetic shielding.

* * * * *